United States Patent
Watts et al.

(10) Patent No.: US 10,507,223 B2
(45) Date of Patent: Dec. 17, 2019

(54) HORIZONTAL AXIS ROTARY SEPARATION APPARATUS AND PROCESS

(71) Applicant: The Original Resinator, LLC, Graton, CA (US)

(72) Inventors: James Eugene Watts, Willits, CA (US); Travis Jeremy Arnovick, Graton, CA (US)

(73) Assignee: The Original Resinator LLC, Graton, CA (US)

( * ) Notice: Subject to any disclaimer, the term of this patent is extended or adjusted under 35 U.S.C. 154(b) by 14 days.

(21) Appl. No.: 15/641,254

(22) Filed: Jul. 4, 2017

(65) Prior Publication Data

US 2018/0008656 A1 Jan. 11, 2018

Related U.S. Application Data

(60) Provisional application No. 62/358,988, filed on Jul. 6, 2016.

(51) Int. Cl.

| | |
|---|---|
| *A61K 36/00* | (2006.01) |
| *A61K 36/185* | (2006.01) |
| *B01D 11/02* | (2006.01) |
| *B07B 1/22* | (2006.01) |
| *B07B 1/24* | (2006.01) |
| *B07B 1/18* | (2006.01) |
| *A23L 3/36* | (2006.01) |
| *A23L 3/37* | (2006.01) |
| *A23L 3/375* | (2006.01) |
| *B07B 7/06* | (2006.01) |
| *B07B 9/00* | (2006.01) |
| *B01D 45/16* | (2006.01) |
| *B01D 46/26* | (2006.01) |
| *B01D 46/30* | (2006.01) |
| *B01D 50/00* | (2006.01) |
| *F25D 3/11* | (2006.01) |
| *A23L 3/44* | (2006.01) |
| *F26B 25/00* | (2006.01) |

(52) U.S. Cl.
CPC .............. *A61K 36/00* (2013.01); *A23L 3/36* (2013.01); *A23L 3/361* (2013.01); *A23L 3/37* (2013.01); *A23L 3/375* (2013.01); *A23L 3/44* (2013.01); *A61K 36/185* (2013.01); *B01D 11/02* (2013.01); *B01D 11/0226* (2013.01); *B01D 11/0246* (2013.01); *B01D 11/0273* (2013.01); *B01D 45/16* (2013.01); *B01D 46/26* (2013.01); *B01D 46/30* (2013.01); *B01D 50/002* (2013.01); *B07B 1/22* (2013.01); *B07B 1/24* (2013.01); *B07B 7/06* (2013.01); *B07B 9/00* (2013.01); *F25D 3/11* (2013.01); *A61K 2236/30* (2013.01); *B01D 2273/28* (2013.01); *F26B 25/005* (2013.01)

(58) Field of Classification Search
CPC .............. A61K 2236/00; A61K 36/185; A61K 2236/30; A61K 36/00; B01D 11/0273; B01D 11/0246; B01D 11/0226; B01D 11/02; B01D 45/16; B01D 46/30; B01D 46/26; B01D 50/002; B01D 2273/28; B07B 1/18; B07B 1/22; B07B 1/24; B07B 9/00; B07B 7/06; F25D 3/11; F26B 25/005; A23L 3/44; A23L 3/375; A23L 3/361; A23L 3/36; A23L 3/37

See application file for complete search history.

(56) References Cited

U.S. PATENT DOCUMENTS

| | | |
|---|---|---|
| 3,079,761 A | 3/1963 | Toulmin, Jr. |
| 3,446,030 A * | 5/1969 | Rubin .................... A23L 3/375 62/379 |
| 4,051,771 A | 10/1977 | Miyata et al. |
| 4,137,723 A | 2/1979 | Tyree, Jr. |
| 4,154,021 A | 5/1979 | Griffith |
| 4,157,061 A | 6/1979 | Margus, Jr. |
| D280,628 S | 9/1985 | Besson |
| 4,795,651 A | 1/1989 | Johnson et al. |
| 4,953,365 A * | 9/1990 | Lang ..................... A23L 3/361 198/778 |
| 5,964,100 A | 5/1999 | Wisniewski |
| 6,158,591 A | 12/2000 | Delp |
| 7,008,528 B2 | 3/2006 | Mitchell et al. |
| 8,640,877 B1 | 2/2014 | Pastorius |

(Continued)

FOREIGN PATENT DOCUMENTS

WO 200400919 A2 1/2014

OTHER PUBLICATIONS

"Home-made hash", by Wombat, dated Mar. 8, 2005, downloaded from <http://www.poUv/video/2005/03/08/4117/>.

(Continued)

*Primary Examiner* — John Kim
(74) *Attorney, Agent, or Firm* — Edward S. Sherman

(57) ABSTRACT

A horizontal axis rotary separation apparatus is deployed in a process for separating resinous trichomes rich in flavoring, aromatic and/or medicinal components produced in plant trichome glands from unwanted plant matter. The process physically separates resin rich beads at the trichome gland head from extraneous plant matter by one or move separation sieves. The sieves are provided in or as a casing over a rigid frame member. The sieves are mesh fabric bags or screen that are easily opened and replenished in a batch operating mode, and are removable from the frame for cleaning and maintenance. Other aspects of the invention include processes that improve process efficiency and speed, and yield products of superior quality.

22 Claims, 12 Drawing Sheets

(56) References Cited

U.S. PATENT DOCUMENTS

| | | |
|---|---|---|
| D706,324 S | 6/2014 | Watts |
| 8,955,687 B1 | 2/2015 | Dews et al. |
| 9,066,910 B2 | 6/2015 | Rosenblatt et al. |
| 2009/0250383 A1 | 10/2009 | Young et al. |
| 2010/0119606 A1 | 5/2010 | Whittle et al. |
| 2004/0271940 | 9/2014 | Wurzer |
| 2014/0271940 A1 | 9/2014 | Wurzer |

OTHER PUBLICATIONS

"Inside the Trichome", by Bubbleman and Jeremiah Vandermeer, published on Cannabis Culture on Jun. 12, 2009.
PCT Search report in PCT/US2018/064036, dated Mar. 7, 2019.
Youtube video at URL:https://www.youtube.com/watch?v=BQuxTFugMoc, currently dated as Sep. 1, 2015 at the URL The attachment includes what are believed to be the most material still images from this video sequence.
Youtube video at URL:: https://www.youtube.com/watch?v=1zJiVnVdxdM, currently dated as Sep. 16, 2016 The attachment includes what are believed to be the most material still images from this video sequence.
https://www.youtube.com/watch?v=Gb03Xm4yRL0, currently dated at this URL as Jun. 2, 2016 The attachment includes what are believed to be the most material still images from this video sequence.
Webpage from www.pollinator.nl, retrieved prior to Jul. 6, 2016.

\* cited by examiner

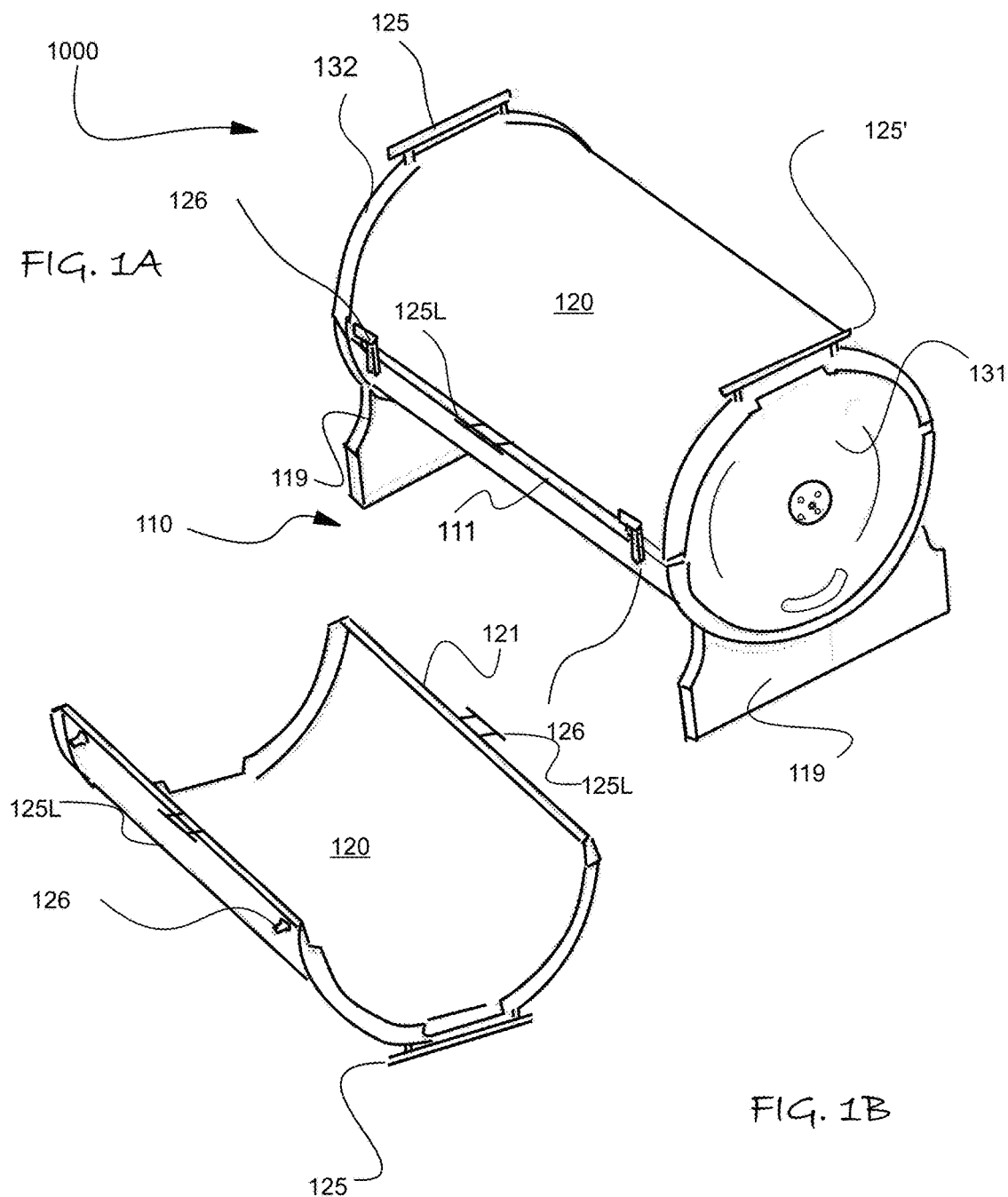

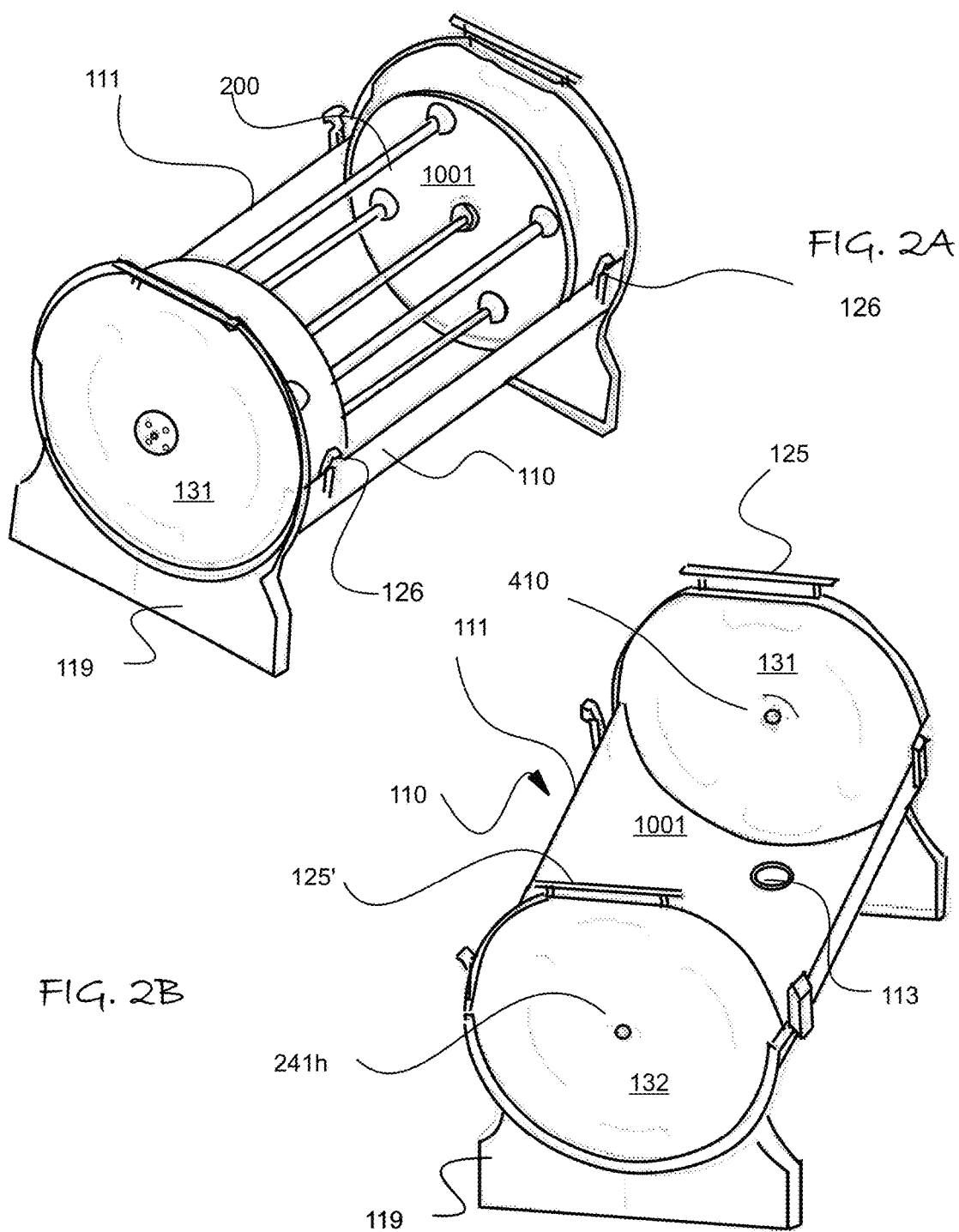

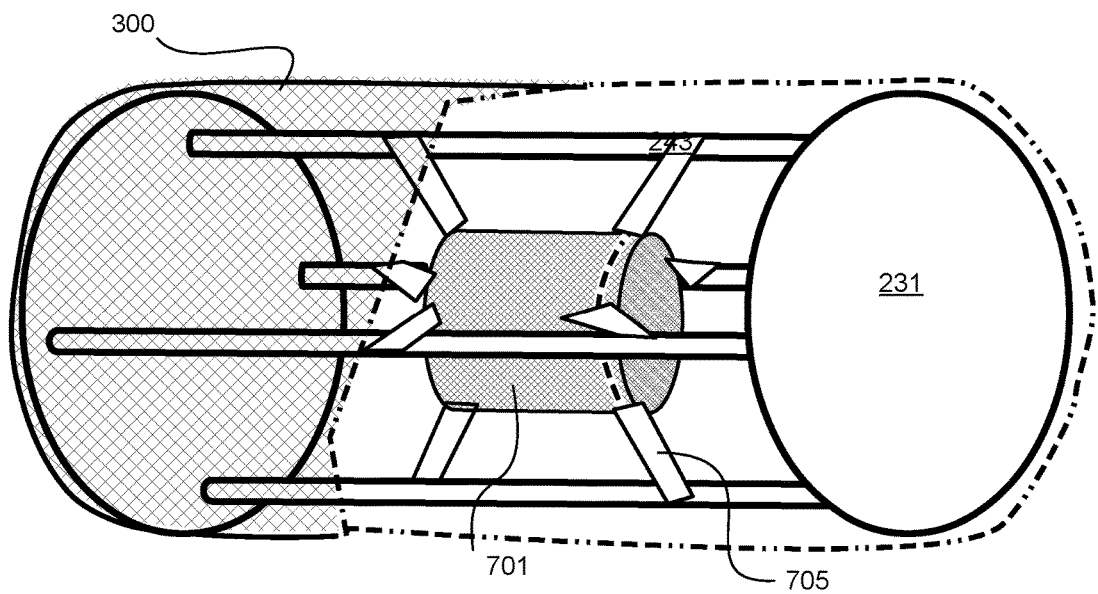
FIG. 10B
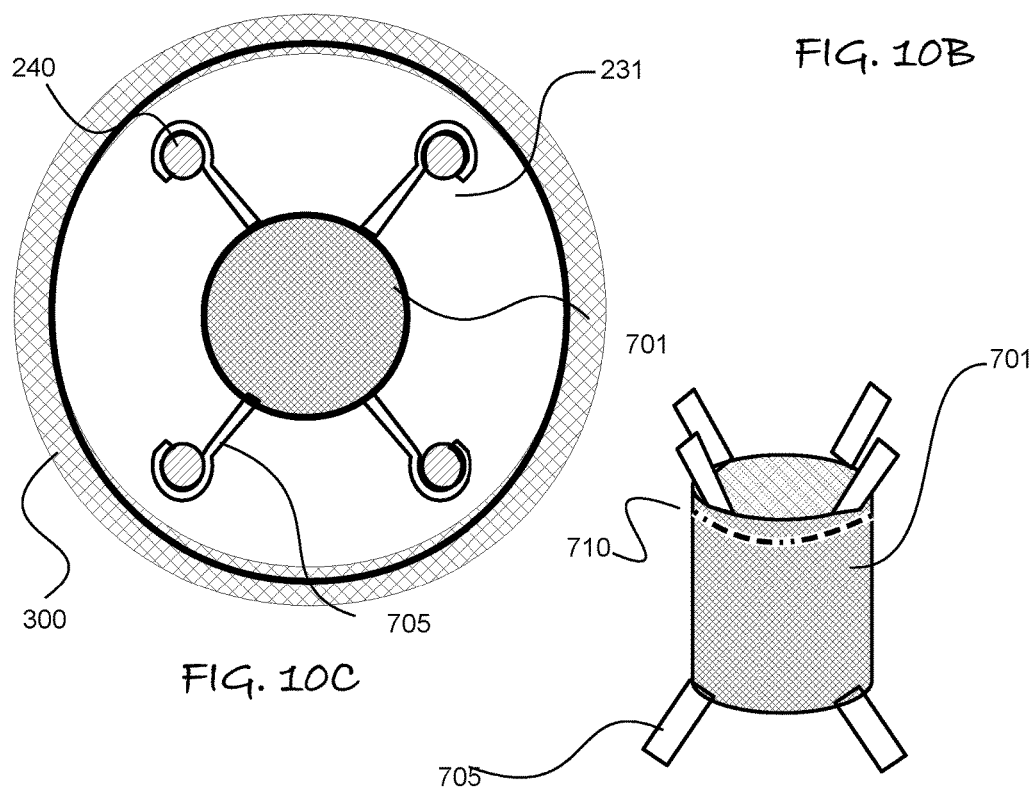
FIG. 10C
FIG. 10A

HORIZONTAL AXIS ROTARY SEPARATION APPARATUS AND PROCESS

CROSS REFERENCE TO RELATED APPLICATIONS

The present application claims the benefit of priority to the U.S. Provisional Patent Application of the same title that was filed on Jul. 6, 2017, having application no. 62/358,988 and is incorporated herein by reference.

BACKGROUND OF INVENTION

The field of the present invention is the extraction of resins containing organic compounds from resinous plants, and more particularly to the separation of resin from resin-bearing glandular trichomes bearing from plants buds and flower, which tend to be high in trichome as a weight and/or volume, as well lower weight resin bearing plant matter, such as leaves and stem materials.

A number of plant varieties produce commercially valuable isoprene derivatives and phenolic compounds such as terpenoids in cell assemblies know as trichomes or more specifically, in the glands of glandular trichomes. Portions of different plants are rich in trichomes containing compounds of interest in commercial and medicinal applications. Conventional extractive processes may not be adequate in preserving volatile and/or oxidation-sensitive compounds.

Conventional extraction and separation methods utilize solvents which may be polar, non-polar or combinations thereof in order to extract and separate desirable substances. Conventional extraction methods are expensive to conduct safely and may introduce undesired compounds by collateral extraction. Commonly extracted undesirable compounds may include pigments such as anthocyanin, chlorophyll, tannins, saponins and lipids from cellulosic materials.

Further, as plants mature, many glands of glandular trichomes increase in size, mass and chemical composition. Plant cells associated with the trichomes biosynthesize phenolic compounds including terpenoids such as cannabinoids and humulones, However, at harvest time, when the plant is deemed to have reached a peak in the content of desired compounds, trichome assemblies may be in a range of sizes. Trichome and trichome gland assemblies can be separated from the bulk of undesirable plant material by sieving procedures. Larger trichomes can be harder to separate from undesirable plant matter that does not contain desired chemical species.

However, as resin bearing trichomes are sticky, physical separation by dry or wet sieving processes are problematic because a large fraction of plant matter fragments of comparable size to the desired trichomes are generated from the mechanical force of agitation, chopping or grinding of the plant matter to release the desirable trichomes and/or trichome glands.

In any physical separation process, it is necessary to not only collect the resin product, but remove residue and clean the filter.

It is an object of the present invention to provide an improved process and device to remove residue and clean the filter, as well as collect the product under conditions discovered most conducive to rapid and efficient separation.

The above and other objects, effects, features, and advantages of the present invention will become more apparent from the following description of the embodiments thereof taken in conjunction with the accompanying drawings

SUMMARY OF INVENTION

In the present invention, the first object is achieved by providing Another aspect of the invention is a any of the aforesaid methods A horizontal axis rotary separation apparatus comprising a cylindrical chamber having a lower half cylindrical basin with an upper rim and having a first and second circular end plates coupled to opposing end of lower half cylindrical basin that extend above the upper rim, an upper half cylindrical lid with a lower rim, adapted for connecting to the upper rim and an upper periphery of the first and second circular end plates that extends above the upper rim, a rotating filter support frame adapted to rotate about a cylindrical axis thereof to provide a cylindrical cavity defined by a connected upper and lower cylindrical base, a removable filter member adapted to form an enclosed space over the filter support frame, a rotary drive means adapted to rotate the opposing ends of the rotary support frame in the first and second circular end plates, and a rotary drive coupling to support opposing ends of the rotary support frame in the first and second circular end plates.

A second aspect of the invention is such a horizontal axis rotary separation apparatus wherein the upper half of the cylindrical lid is coupled to the lower half cylindrical base by one or more hinges disposed at an adjacent portion of the upper and lower rims thereof, the hinge being disposed for adjacent placement of the upper half to the lower half.

Another aspect of the invention is any such a horizontal axis rotary separation apparatus wherein the removable filter member has longitudinal side zipper that extends substantially between the upper and lower cylindrical base.

Another aspect of the invention is any such a horizontal axis rotary separation apparatus wherein the removable filter member has a circumferential reinforcement band disposed between opposing ends.

Another aspect of the invention is a method of plant matter separation comprising the steps of providing at least a first horizontal axis rotary separation apparatus, having a chamber having an inlet port and an outlet at a bottom, a rotating filter support frame adapted to rotate about a cylindrical axis thereof to provide a cylindrical cavity defined by a connected upper and lower cylindrical base, filter member adapted to form an enclosed space over the filter support frame wherein the inlet port is adopted to deliver product to be separated into the enclosed space, a rotary drive means adapted to turn the rotating filter support frame while a primary axis thereof is disposed in a horizontal orientation, admitting plant matter to the enclosed space of the first horizontal axis rotary separation apparatus, rotating the rotating filter support frame of the first horizontal axis rotary separation apparatus, admitting at least one of water, dry ice, liquid carbon dioxide and liquid nitrogen to the enclosed space during, collecting a purified effluent from the outlet at the bottom of the chamber of the second horizontal axis rotary separation apparatus.

Another aspect of the invention is a such a method wherein the at least one of water, dry ice, liquid carbon dioxide and liquid nitrogen is admitted to the enclosed space during occurs before the step of turning the rotating filter support frame of the first horizontal axis rotary separation apparatus.

Another aspect of the invention is a method of plant matter separation comprising the steps of providing a first and second horizontal axis rotary separation apparatus, each having; a chamber having an inlet port at the side and an outlet at a bottom, a rotating filter support frame adapted to turn in rotary motion about a cylindrical axis thereof to provide a cylindrical cavity defined by a connected upper and lower cylindrical base, a filter member adapted to form an enclosed space over the filter support frame, wherein the inlet port is adopted to deliver product to separated into the enclosed space, a rotary drive means adapted to rotate the rotating filter support frame about a primary axis thereof that is disposed in a horizontal plane, wherein the outlet port of the first horizontal axis rotary separation apparatus is connect to the inlet port of the second horizontal axis rotary separation apparatus, admitting plant matter to the enclosed space of the first horizontal axis rotary separation apparatus, turning the rotating filter support frame of the first and second horizontal axis rotary separation apparatus, collecting a purified effluent from the outlet at the bottom of the chamber of the second horizontal axis rotary separation apparatus.

Another aspect of the invention is a any of the aforesaid methods wherein the filter member of the first horizontal axis rotary separation apparatus has a larger opening size than the filter member of the second horizontal axis rotary separation apparatus.

Another aspect of the invention is a any of the aforesaid methods wherein a liquid freezing agent is injected into enclosed space over the filter support frame of the first horizontal axis rotary separation apparatus and water is then injected to flush a product from the first outlet port to an inlet port of the second horizontal axis rotary separation apparatus.

Another aspect of the invention is a any of the aforesaid methods further comprising using a one or more of dry ice and balls to improve agitation in enclosed space over the filter support frame of the second horizontal axis rotary separation apparatus.

Another aspect of the invention method of processing plant matter, the method comprising providing a mixture of plant matter that includes flower and flower buds and at least one of leaves, bracts and bracteoles, flowers and buds containing calyxes and sugar leaves, placing the mixture in a contained spaced bounded on at least one side by a mesh member, wherein the mesh member has a spacing sufficient to retain the mixture of plant matter, tumbling the mixture within the closed space, introducing a liquid freezing agent into the closed space, wherein residual moisture in the one or more of the leaves, bracts and bracteoles freezes causing the fragmentation thereof such that the fragmented plant matter traverses the mesh member and the closed space retains a residual portion of the flowers.

Another aspect of the invention is any of the aforesaid methods wherein the plant matter is from the species cannabis and the residual portion is primarily calyxes.

Another aspect of the invention is a any of the aforesaid methods wherein the fragmented plant matter includes one or more of fan leaves and sugar leaves.

Another aspect of the invention is a any of the aforesaid methods wherein the contained space is a cylinder having a first circular plate at a top and a spaced apart second circular plate as a bottom, wherein the first and second circular plate are connected by a cylindrical wall that is at least partially covered by the mesh member.

Another aspect of the invention is a any of the aforesaid methods wherein the circular top and bottom are connected by spaced apart rods disposed between a center of the cylinder and the cylindrical wall.

Another aspect of the invention is a any of the aforesaid methods further comprising a step of adding balls to the contained space to facilitate the tumbling of the mixture Another aspect of the invention is a any of the aforesaid methods wherein one of the liquid carbon dioxide and liquid nitrogen are introduced to the enclosed space as a jet from a center of one of the first and second circular plate wherein the jet of an expanding gas impinges on the other circular plate to disperse within the plant matter.

Another aspect of the invention is a any of the aforesaid methods wherein the cylinder is rotated to tumble the plant matter.

Another aspect of the invention is a any of the aforesaid methods wherein the mesh member has holes with a diameter of about 0.25 inches Another aspect of the invention is any of the aforesaid methods further comprising the additional steps of: terminating the tumbling of the plant matter, removing the remaining plant matter that consists essentially buds and flower, and further processing the buds and flower to remove resin bearing trichomes there form.

The above and other objects, effects, features, and advantages of the present invention will become more apparent from the following description of the embodiments thereof taken in conjunction with the accompanying drawings.

BRIEF DESCRIPTION OF DRAWINGS

FIG. 1A is a perspective view of the separator with the lid in place, whereas

FIG. 1B shows the inside of the lid in a removed inverted position from FIG. 1A.

FIG. 2A is a top perspective view of the lower portion of the separator with the lid removed to illustrate an embodiment of the frame, whereas FIG. 2B is a perspective view of the separator showing the frame and lid removed.

FIG. 5A is a perspective view of an embodiment of the filter installed over the frame while

FIG. 8A is a side elevation view of another embodiment of the filter, while

FIG. 8B is a cross-sectional elevation view of a portion of the filter that attaches to the frame, whereas FIG. 8C illustrates the filter in a disassembled condition in a plan view.

FIG. 10A is a perspective view of an internal filter bag whereas FIG. 10B and 10C illustrate in a perspective view and cross-sectional view respectively how the bag is mounted within the frame to be surrounded by the larger filter that fits over the frame.

DETAILED DESCRIPTION

Figure 3A:
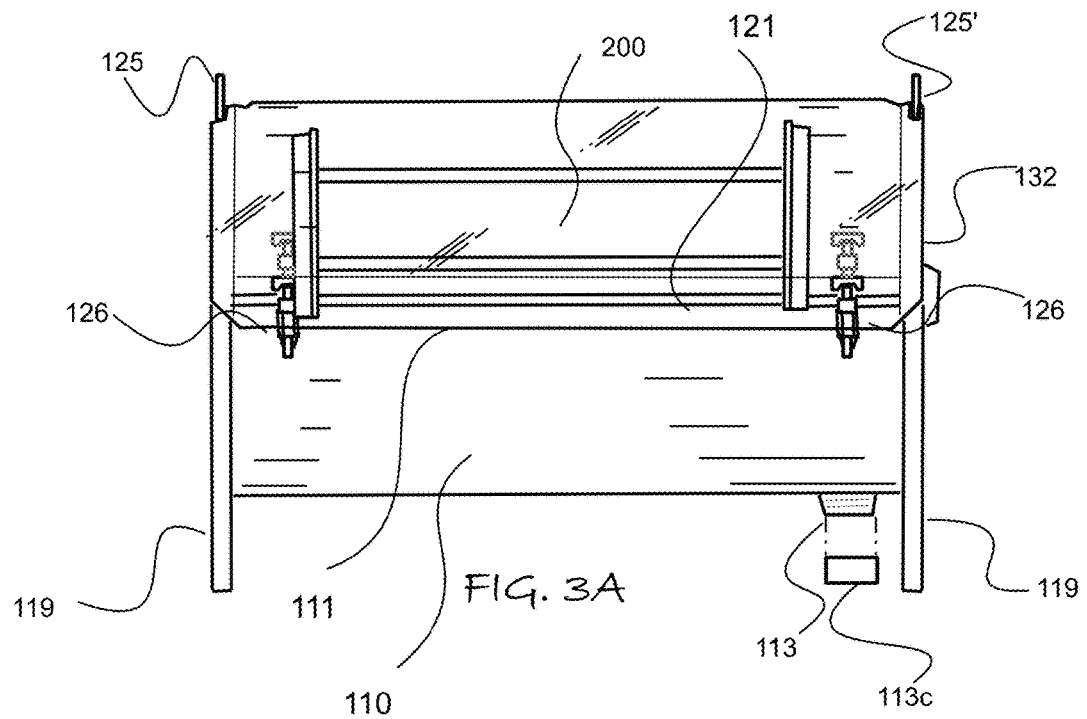
FIG. 3A is a side elevation view of the separator with a transparent lid.

Referring to FIGS. 1A through 12, wherein like reference numerals refer to like components in the various views, there is illustrated therein a new and improved Horizontal Axis Rotary Separation Apparatus and Process, generally denominated 1000 herein.

In accordance with an aspect of the present invention the horizontal axis rotary separation apparatus 1000 comprises a chamber 100 which may have a half cylindrical basin 110 having an upper rim 111 and a half cylindrical lid 120 having a lower rim 121. The basin 110 preferably includes at a bottom a drain portal 113 to remove fluid used in the separation process and/or the resinous product of the separation process. The basin 110 is preferably disposed above a support surface by feet or frame edges 119. In such an embodiment the chamber 110 is cylindrical. However, the chamber 110 can be other shapes so long as it accommodates the internal rotating filter support frame 200, described further below. Other aspects of the invention will be described with respect to the preferred cylindrical chamber 100.

A pair of side end plates 131 and 132 is connected to opposing ends of the basin 110 and extends upward above the upper rim 111 thereof. The lid 120 is configured to fit over the edge of the side plates 131 and 132 so the straight side of the lower rim 121 meet the corresponding straight sides of the upper rim 111 and generally provide a closed cylindrical cavity 1001. The sides 131 and 132 may have upward extending handles 125 and 125'. The lid 120 preferably has handles 125L just above the opposing lower rims 121. Handles 125 and 125' are also optionally placed on the adjacent portion of the lid 120, as illustrated when the lid is inverted in FIG. 3B. In either embodiment, the lid 120 may also have handles 125L just above the opposing lower rims 121. The junctions between the basin 110 edges and the edges of the side end plates 131 and 132 that mate with the edge of the lid are preferably at least partially sealed during processing with a gasket or conforming elastic material, which is optionally discrete pieces of convention weather stripping material.

The cylindrical cavity 1001 between the basin 110 and lid 120 also contains a rotating filter support frame 200. The filter support frame 200 has attached spaced apart support disks 231 and 232 that are connected by a series of posts 240 to form a rigid support assembly. Three or more posts 240 extend about the periphery 231p of each disk 231 and 232 to form a rigid support for a generally but not exclusively flexible filter bag member 300, of which an embodiment is illustrated in perspective view in FIG. 3A. The support frame 200 optionally includes a central post or support 241, which in select embodiments provide a conduit to 241b feed fluid, such as gas or liquid into the cavity 1001 via side holes 241h to aid in the separation process. Post 241 is disposed along the cylindrical axis of the frame 200, which becomes the rotary axis in the process of separation.

The rotating filter support frame 200 is adapted to rotate about a cylindrical axis 201 of the device 1000 and the cylindrical cavity 1001. A rotary drive means 400 is adapted to couple to at least one end of the rotary support frame 200. The filter frame support 200 has portions 242 and 243 that extend beyond spaced apart support disks 231 and 232 that engage a rotary drive couplings 500 supported by the by the side plates 131 and 132. At least one of the rotary drive couplings is preferably a rotary bearing with an intermeshing or rotary tooth structure 410 at one side to engage a complimentary structure in the outward extending portion 242 or 243. The rotary drive means 400 is coupled to the rotary tooth structure 410, such as by a drive shaft that is support by a bearing at the interface to the side plates 131 or 132. The opposing side plate also has a rotary bearing for supporting the other extending post 242 or 243. The rotary tooth structure 410 is preferably disposed inside the cavity 1001. It is also preferably to deploy a rotary bearing and quick disconnect on one end outside of support disks 231 or 232.

The removable filter member 300 extends over the support frame 200 and is adapted to be filed with plant matter from a side opening having a zipper 310. In the process of use, plant matter is inserted in the removable filter member 300 and with the lid 120 removed. The lid 120 is closed to seal the cavity 1001 and the latching hinges 126 are engaged to secure the lid 120 in place. Then the filter support 200 is rotated by the rotary drive means 400. Plant resin particles escape through the filter openings and tumble to the bottom of the basin 120. The lid 120 is opened and the rotary filter support frame 200 is removed from the rotary coupling, such as the rotary tooth structure 410 in the lower cylindrical base 120, and then placed in the inverted half cylindrical lid 120. When the frame 200 is removed solid product is optionally removed from the bottom of the basin 120 via the rim 121, or via the drain portal 113. Fluid can be used to continuously flush product through the drain portal 113.

Figure 3B:
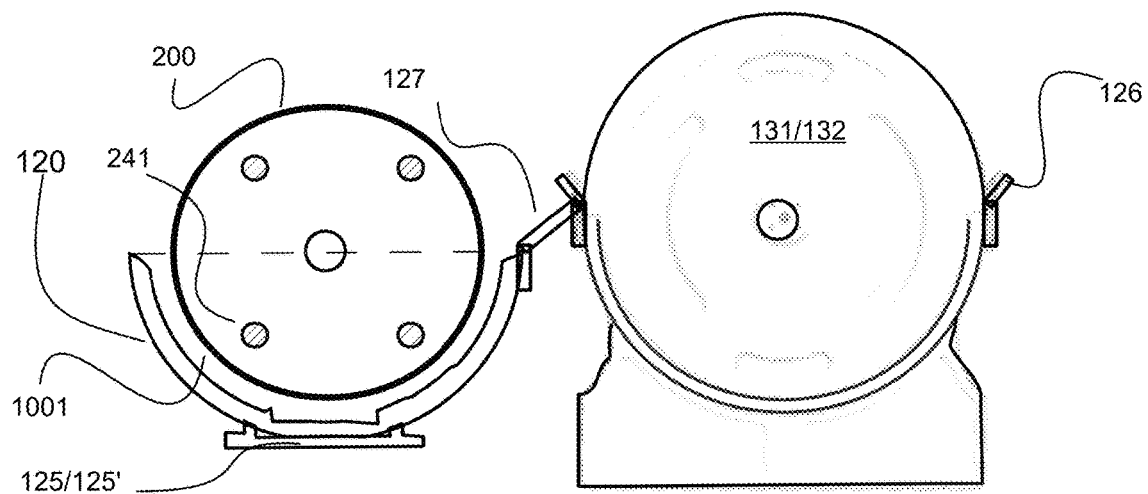
FIG. 3B shows the separator in an orthogonal side elevation view with the lid open and inverted.

In a more preferred embodiment illustrated in FIG. 3B, the lid 120 is in hinged engagement to the side of the basin 120 to provide a work station for removing and replacing the filtered plant matter with new plant matter while the product is being removed from the basin 120. As illustrated in FIG. 3B, the latches on one side of the rim 111 are preferably double axis hinges 127 to space the upper shell or lid 120 laterally away from the lower shell or basin 110. The lid 120 has handles 125 and 125', which support the lid 120 in the inverted position used to support the filter member 300 as disposed over the support frame 200. The rims 121 and 111 opposite the hinges 126 and 127 are connected by clamps prior to engaging the rotational drive means 400.

Another aspect of the invention are preferred and alternative embodiments of the removable filter member 300, which are adapted to fit over the rotating filter support frame 200, which more particularly can be readily removed or replaced from the support for cleaning or maintenance, or simply to facilitate the removal of spent plant matter after resin product is removed.

It should be appreciated that the filter member 300, such as is illustrated in FIG. 4A-4D, is a generally cylindrical mesh bag generally conforming with the shape of the frame 200 to fill cavity 1001, but configured to not interfere with the rotation of the frame 200, as well as to provide a tight seal to the support disks 231 and 232 for maintaining plant matter therein during the separation process. The bag or filter 300 has a rectangular central portion 305 that is formed into a tube sealed by circular ends or bases 331 and 332. As illustrated in FIG. 5A and 5B, when the filter 300 extends over the support disks 231 and 232 the circular ends 331 and 332 are preferably annular to provide an aperture 335 for extending post 242 or 243. The annular ends 331 and 332 are optionally tightened over the support disks 231 and 232 by a cinch cord 383 or elongated elastic member that passes through a channel formed in the inner annular end of each of end 331 and 332. The filter member on the support frame 200 defines within the closed interior surface thereof and disks 231 and 232 a container or containment vessel 311 for materials to be processed of which a smaller component, or a component produced or released during processing will exit the container 311 and enter the surrounding portion of the closed cylindrical cavity 1001, for eventual collection with the lid and filer frame 200 removed or by exiting by drainage port 113.

In some processes of use it is desirable to add fluid or gases in to cavity 1001 or the container 311 while the cover is in placed and optionally when the support frame 200 is turning or rotating. Such inlet for fluid and gases can be in the center of the end 131 or 132, passing through the adjacent end of disk 231 and 323 at the center thereof to introduce gas or fluid into the container 311 to aid in the process of the matter therein. Fluid can be introduced by the same method or any other penetration in the chamber 100 to flush material that exit the container 311 via the drainage portal 113.

It should be appreciated that the longitudinal side zipper 310, which is deployed for side filling access to the frame supported filter 300, can be replaced with an alternative sealing means, such as loop and hook fasteners, button, loops, snaps and the like. Side zipper 310 is generally formed by attaching the engaging side teeth 310a and 310b at sides 301a and 301a' of the rectangular screen or mesh sheet 305.

Figure 6:
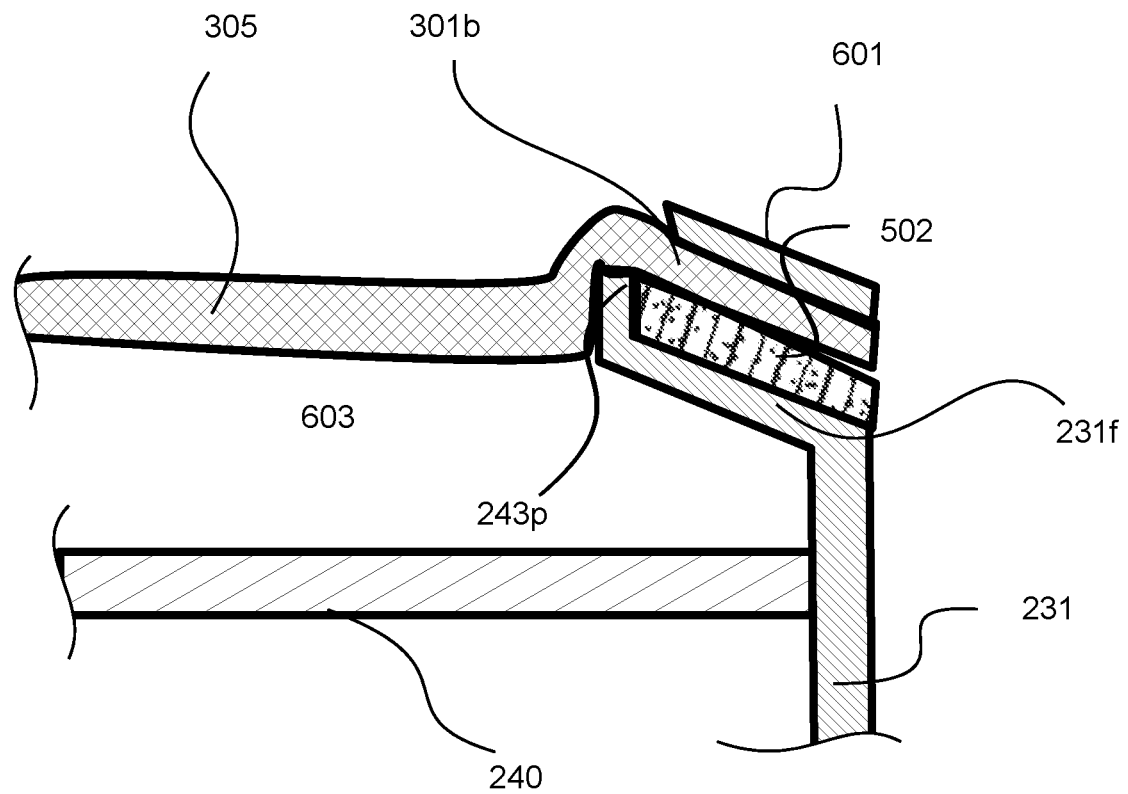
FIG. 6 is a cross-sectional elevation view of another embodiment of the filter shown attached the ends of the support frame.

As shown in FIG. 6, the filter 300 can be formed by attaching the rectangular filter sheet 305 to the annular flange like ends 231f of the disks 231 and 232 by a clamp means, such as a strap or tightened belt member 601 that compresses the edge 301b of the rectangular sheet 305 into a foam member 502 that is either adhered to or supported by disk 231/232. The compressed foam 502 prevents leakage of product from inside the filter 300 at edges 301b and 301b'. The ends of the belt 601 can be attached with a buckle, hook and loop fasteners, snaps and the like.

Figure 7:
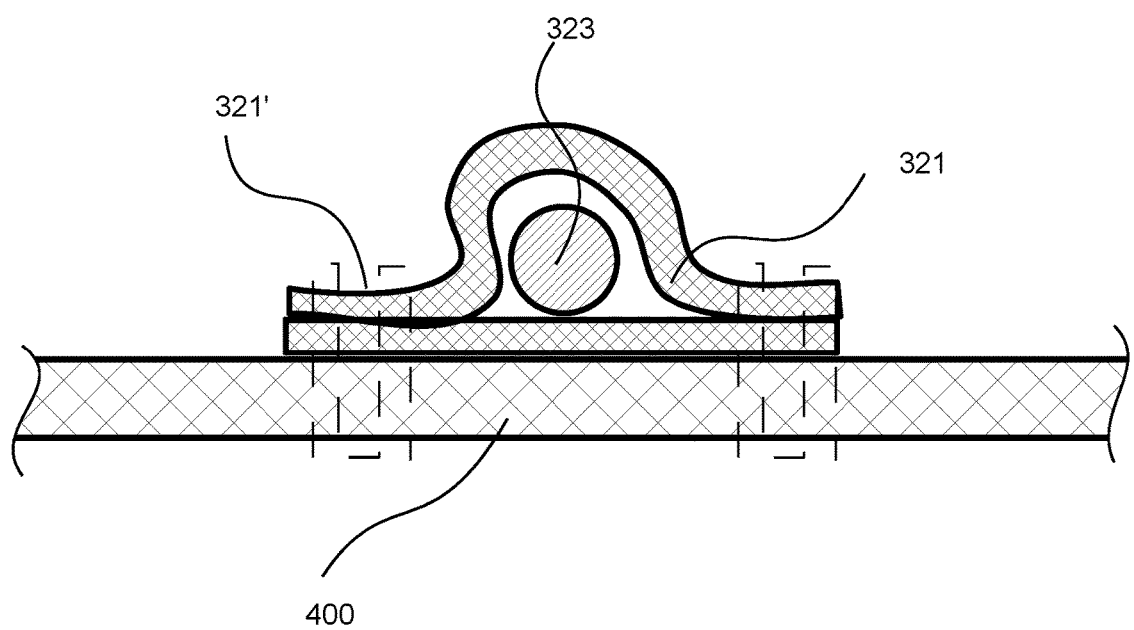
FIG. 7 is a cross-section elevation view through a central portion of the filter that is transverse to a cord showing the surrounding reinforcing strip.
Figure 8:
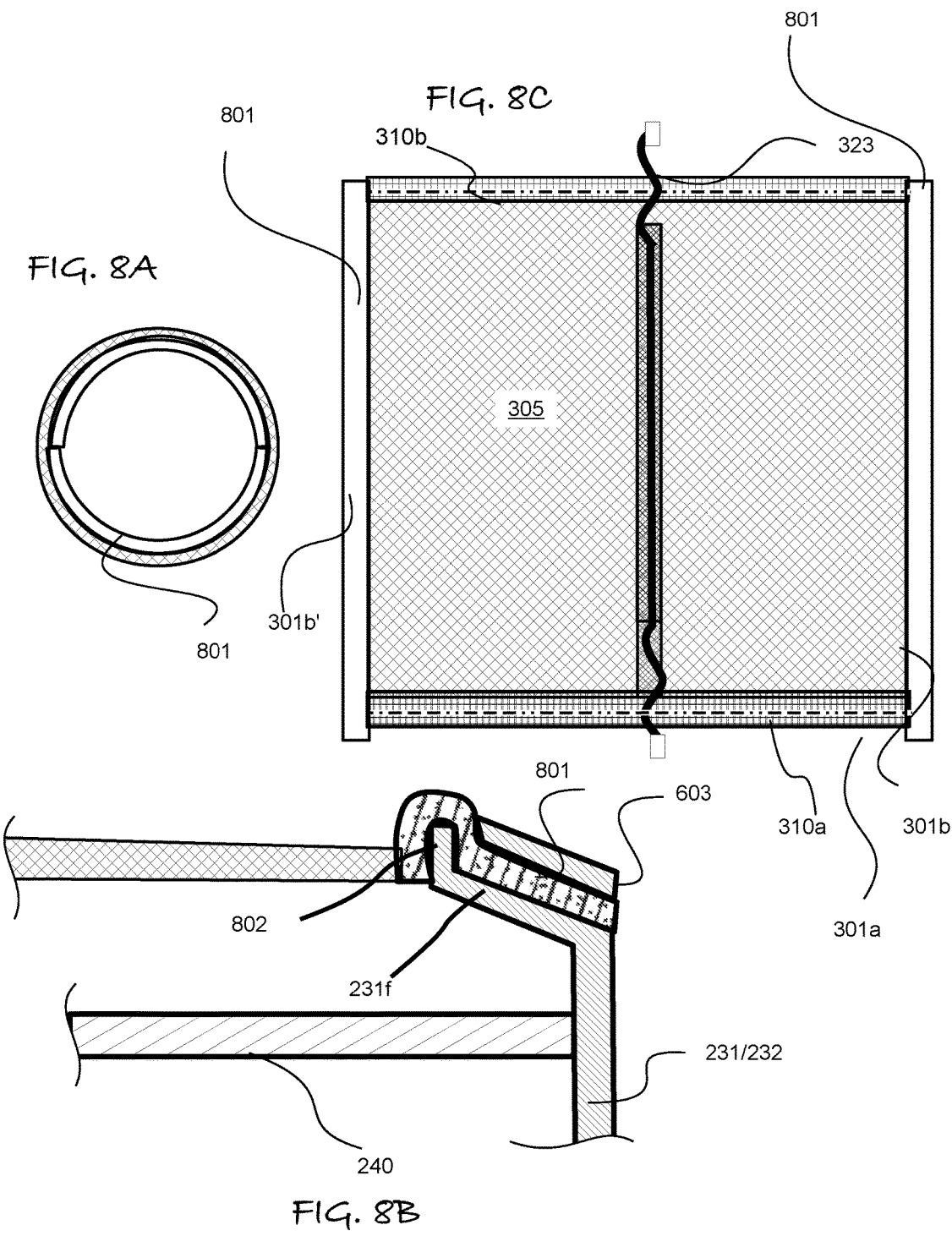

The filter member or bag 300 of FIG. 4-6 has the aforementioned zipper 310 along a longitudinal side may also include one transverse reinforcing band, such as a fabric strip 320 extending around the circumference of the bag disposed between opposing ends. As shown in FIG. 7, the fabric strip 320 is preferably two adjacent strips 321 and 321' sewn together at the edge to the mesh 305 to form an interior channel that receives an elastic cord 323 that is tightened when the zipper 310 is closed. The cord 323 is tightened by drawing the opposing ends through a common clamp member that is closed. It should be appreciated that all zipper pulls preferably have a means to be secured in a closed state, such as a locking zipper, button, snap, loop and hook fabric cover and the like.

Another configuration of the filter 300 is shown in FIG. 8A-C in which a rectangular sheet 305 with side zipper 310 halves at sides 301a and 301a' has attached at each orthogonal ends 301b and 301b' a pairs of clamps members 801, each having a groove 802 adapted to snap into the end support disks 231/232 of the filter support frame 200. A belt 803 is wrapped around the flat portion of the gasket 802 to and tightened around the flange edge 231f such that the filter 300 and support frame 200 becomes an integrated unit. The ends of the belt 803 can be attached with a buckle, hook and loop fasteners, snaps and the like.

Figure 9:
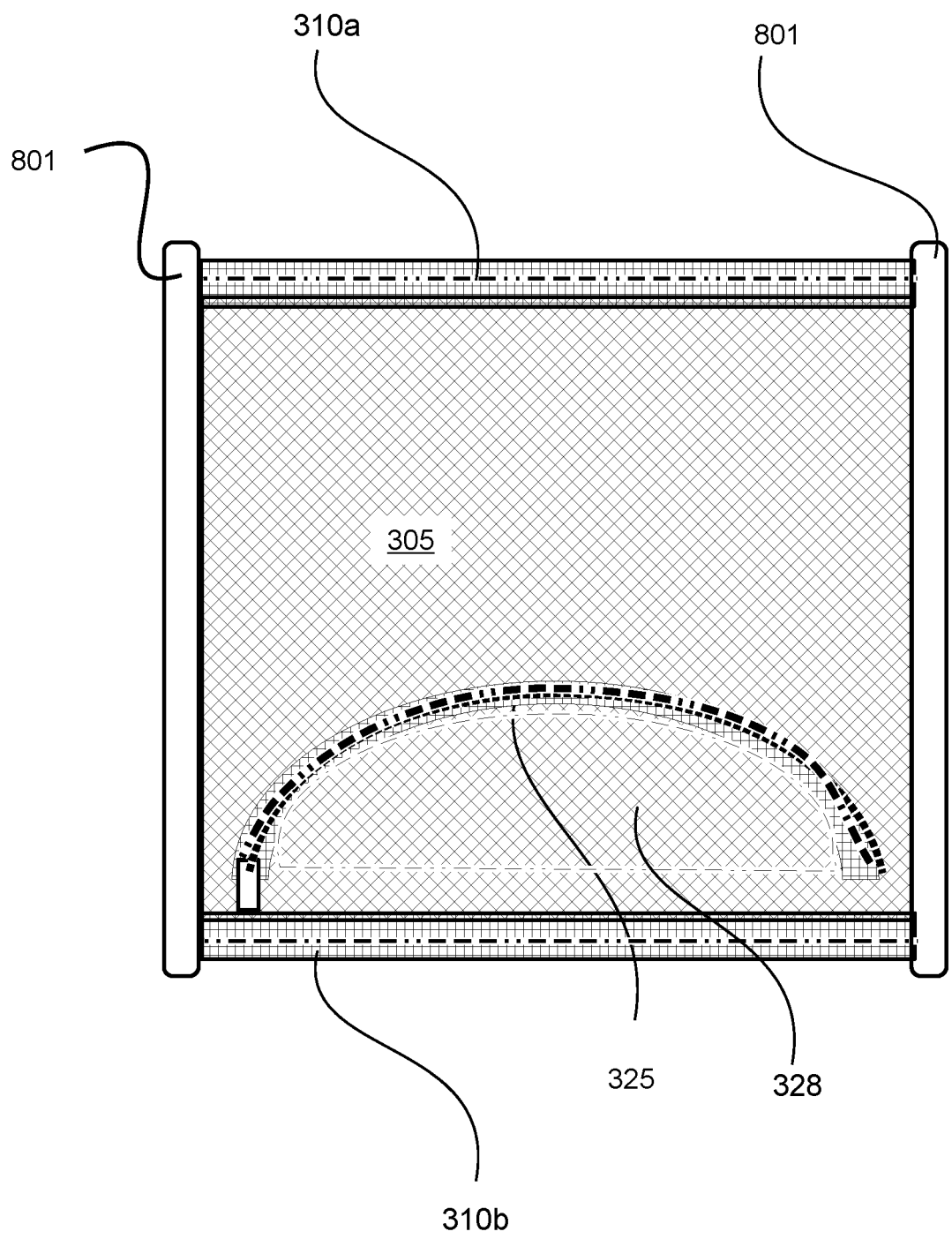
FIG. 9 is a plan view of a portion of another embodiment of the disassembled filter.

FIG. 9 is a top plan view of the filter 300 as in FIG. 8A-C, with a second curved zipper 325 that enables side access to the filter screen sheet 305 when installed integral to the frame 200 via ends 231 and 232, such as when disposed as shown in FIG. 3B, or within the cavity 1001.

It should be appreciated that the posts 240 of the support frame 200 also aid in stirring, tumbling and agitating the plant matter mixture during the separation process, preventing clumping that would lower extraction efficiency and yield. Depending on the nature of the plant matter, and the size of the separation device 1000, the number and shape of the support posts 240 may be varied to further minimize the potential for such clumping. For example, the support posts 240 also may have axially radiating planar fins, cylinder and related protuberances beyond the primary envelope of the post's circular or non-circular shaft diameter to better facility agitation, mixing, tumbling and mechanical disintegration of plant matter to release resin bearing trichromes The drain 113 can also have an external screw thread to accept a removable internally threaded cap 113c, and this cap 113c can be replaced with a hose via a threaded hose coupling to direct the flow of product to different containers or control the output flow rate via valves, such as to match the input rate of rinse water or other fluid.

It should also be appreciated that the outer housing 110 and cover 120 can deviate from the generally cylindrical shape support the inventive filter support assembly 120 that is rotated therein. For example the housing 110 and cover 120 can be an elongated member with any shape linear and curvilinear cross section, including rectangular and square.

The inventive device can also be used to produce compost tea by a least partially filing the chamber portion 12 with water and filing the filter enclosure 300 with composted materials. After sufficient brewing of the compost with agitation by rotating the filter 300 the composted tea is drawn out of the lower exit portal or drain 1131, which during the soaking process, is closed with a valve, cap or plug 113c.

Figure 4A:
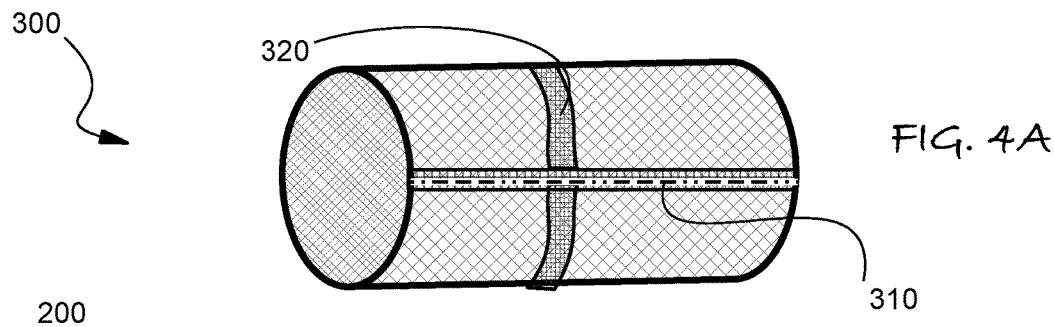
FIG. 4A is a perspective view of an embodiment of the filter, with FIG. 4B illustrating the frame, and FIG. 4.C showing the filter installed over the frame.
Figure 4B:
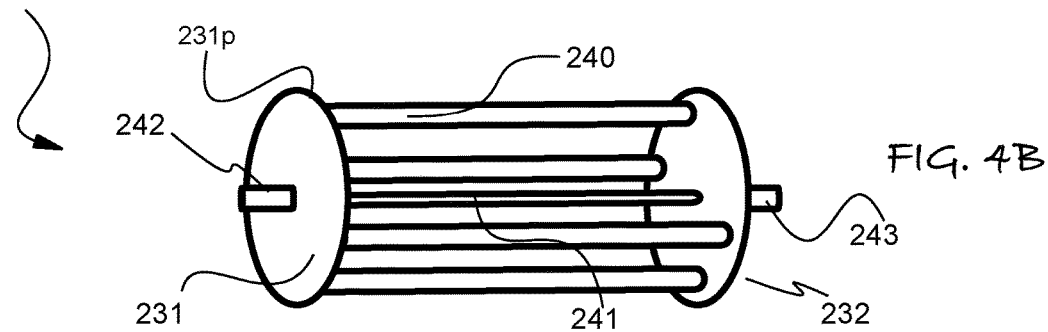
FIG. 4D illustrates the filter in a disassembled condition in a plan view.
Figure 4C:
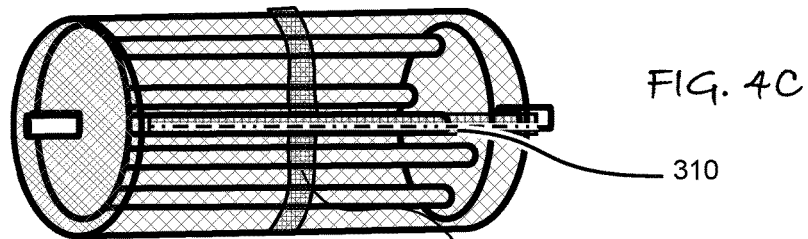
Figure 4D:
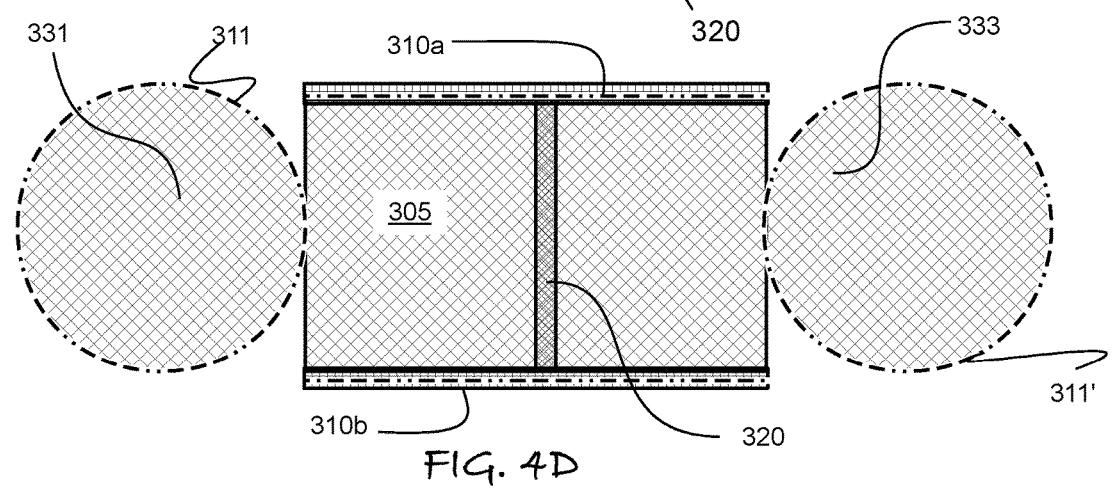
Figure 5A:
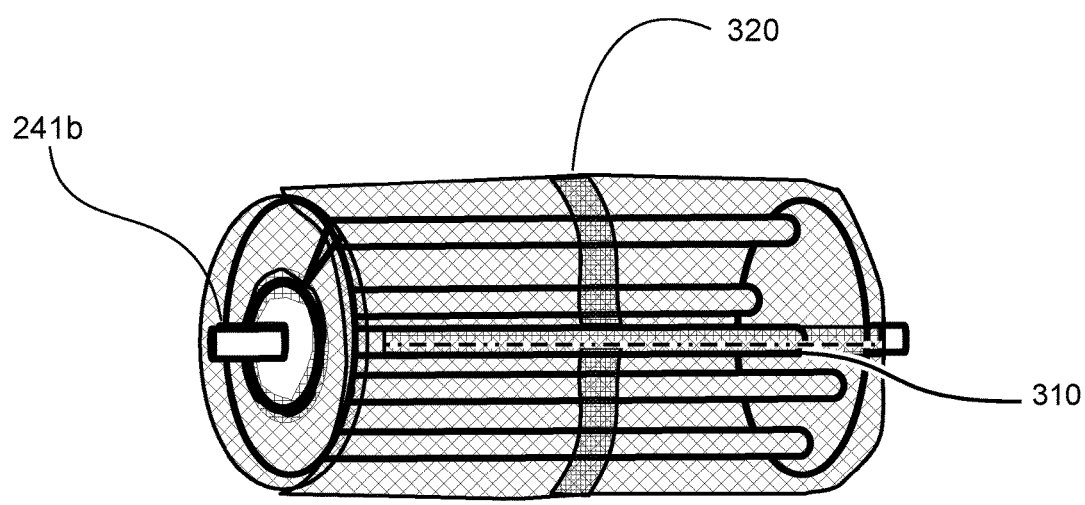
Figure 5B:
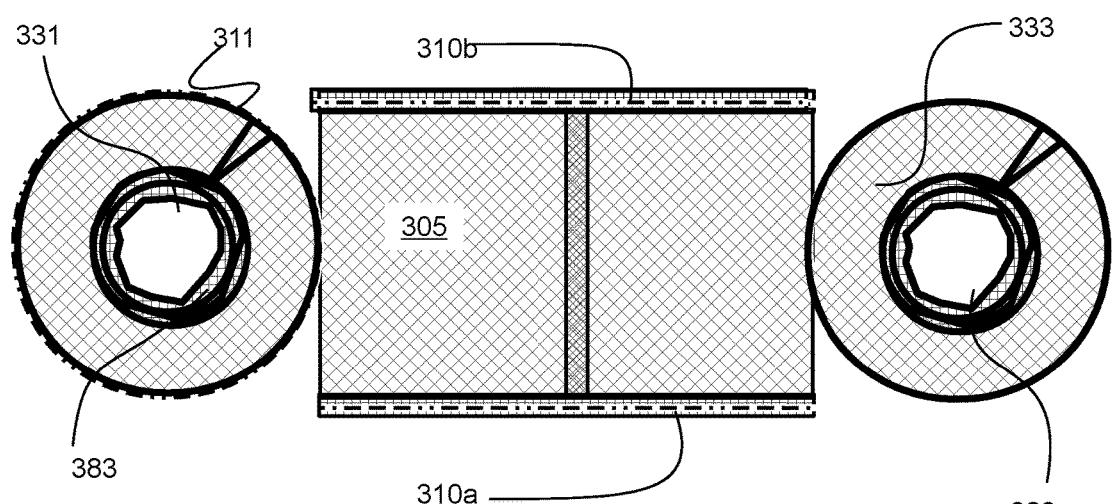
FIG. 5B illustrates the filter in a disassembled condition in a plan view.

The strap or tightened belt member 601 can be used with the other embodiments of the filter 300, and beneficially reduce stress on the primary or side zipper 310, in the embodiment of FIGS. 4d, 5b and 8c, which depending on the size filter can minimize or eliminate the needs for the circumferential cord 323.

The second zipper 329 of FIG. 9 facilities loading and unloading of plant material, as it avoids the strain on the filter bag 300, which would occur if the primary zipper 310 is opened when the separate sides at zipper halves 310a and 310b are pushed away. Further, it facilitates creating a larger opening, as the area circumscribed by the zipper arc 328 opens as a flap.

FIG. 10A is a perspective view of an internal filter bag 701 whereas FIG. 10B and 10C illustrate in a cut-away and cross-sectional view respectively how the bag 701 is mounted within the frame 200 with hooks 705 to be surround by the larger filter 300 that fits over the frame support 200. Bag 701 is a mesh filter with a zipper closure 710. When the outer filter 300 has a finer mesh than the bag 701, the resulting resin particles of a given size are containing within the filter 300, and the bags 701 are repeatedly filled with plant matter until the resin in the filter 300 is ready for removal from the separator 1000.

Figure 11:
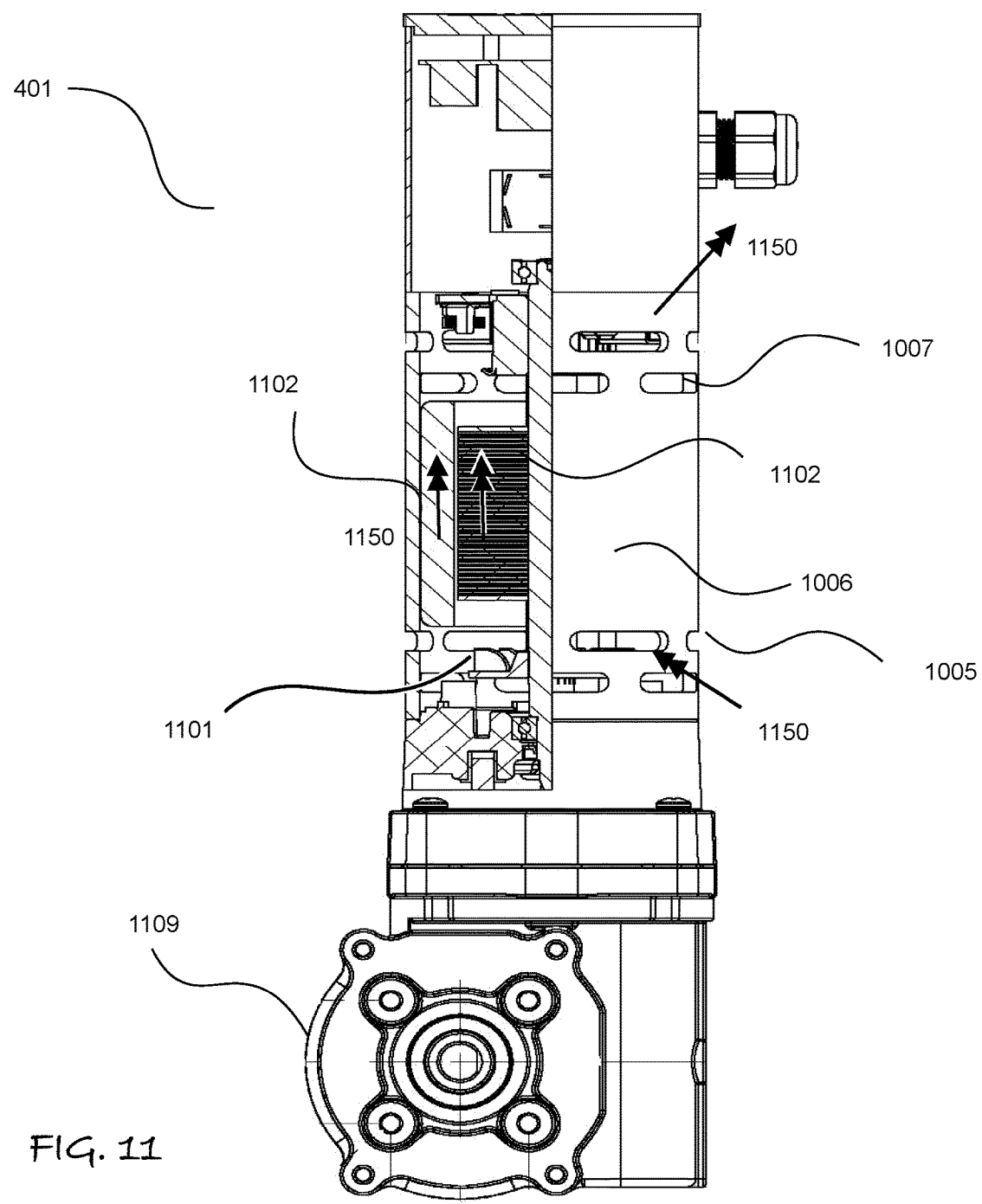
FIG. 11 is a partial cut away elevation view of a preferred embodiment of the motor.

FIG. 11 is a partial cut away elevation view of the preferred embodiment of the drive motor 400 that is a multi process capable motor with wide speed and torque range and motor cooling features. By multi-process we mean capable of carrying out the aforementioned separation processes either dry or wet using an added fluid (generally water, but also ice water slurries) or with the assistance of gas, including adiabatic expansion of carbon dioxide gas to form "dry ice" crystals. The motor's rotor 1103 and stator 1102 are cooled to prevent over heating during use by the fan blades 1101 that coupled to the motor drive shaft, with the fan blades adjacent to intake apertures 1005 formed in the motor housing 1106. The drive shaft that supports the rotor 1103 is connected to the filter support coupling via a gear box 1109. Arrows 1150 show the direction of air flow around the rotor 1003 and between the stator 1102 from the lower intake apertures 1005 to exit at the upper apertures 1007. The forced air cooling is important for providing a single motor that can accommodate the range of speeds and torques needed in the potential separation processes noted above.

The inventive apparatus can be used to separate a wide range and type of materials. Many plant and herb species have the highest concentrations of terpene and cyclic terpene bearing aromatic and medicinal resins in the flowering portions of the plant, and in particular in glandular or secreting trichomes. The flowers typically form at the tips of growing shoots. The flowers, flower buds and leaves have hair like outgrowths that are referred to as trichomes. The glandular trichomes secrete plant resins as a small bulb or head at the end of a stalk like hair.

A range of methods have been developed in attempts to efficiently and economically process Cannabaccae plant matter to extract glandular trichome to yield high concentrations of the resin by separating the plant matter acquired in the harvesting of the flowers, flower buds and leaves from cannabis plants. Some prior art sieving method use water as a medium to suspend the plant matter, while other methods sieve the plant matter without water, while others do so in the dry state. Generally speaking, such wet or water based sieving extraction processes for Cannabaceae trichomes yield an inseparable mix of desirable trichomes and undesirable plant debris, based on size as well as the duration and intensity of agitation. Such a process is generally disclosed in the International Patent Application with publication no. WO 2014/00919A2 (to J. P. Love, which published (January 2014), and is incorporated herein by reference. Another prior art separation method is disclosed in issued U.S. Pat. No. 8,640,877 (Pastorius, Feb. 4, 2014) for a pollen separator, which is incorporated herein by reference. Various raw plant materials are processed via such a water and ice agitation method. It further suggests that small diameter mixtures of plant pollen and plant debris are separated by eight sieves, having progressively smaller holes from 220, 190, 160, 120, 90, 73, 45 to 25 microns. However, the patent is silent on separating the desired pollen or other components from plant debris of the same size, other than by solvent extraction. Similarly, U.S. Pat. No. 4,051,771 (Miyata, et al., Oct. 4, 1977), which is also incorporated herein by reference discloses an apparatus for obtaining lupulin-rich products from hops, in which lupulin glands or trichomes are extracted by a combination of crushing and dry sieving in a frozen state.

The inventive apparatus can be used to separate the trichomes from various plant and herb species. The method of using the apparatus, and variants on the apparatus that might be already known to one of ordinary skill in the art can be adapted to improve the separation rate and efficiency for a particular plan species of separation objective. For example, the inventive apparatus can be used in different ways to obtain either the isolated trichomes, or plant matter having the highest concentration of trichomes. The tips of growing plans that are beginning the flowering process may have multiple flower buds or flower interspersed with fine leaves. These fine leaves are known as bracts and bracteoles. In the case of cannabis and related species, such as hops, the flower region contain multiple buds, also known as calyx's, as well as pistils, seeds, bracts and bracteoles. The bracts and bracteoles in Cannabis are referred to as sugar leaves. While the sugar leaves have higher concentrations of trichomes and the desirable resins than larger or bigger leaves, often referred to as palm leaves, which are lower down the shoots from the flower region, the highest density of trichomes and hence concentration of resins are in the calyx's and pistils of the flowers and buds. Thus, it is desirable in processing Cannabis plants to isolate the flowers from plants, but remove the seeds, if any, and sugar leaves. These sugar leaves, when removed or "trimmed" are frequently referred to as "trim". Another aspect of the invention is a method of rapidly removing the "trim" or "trimming" while leaving the other desirable portions of the plant, which is the flower and buds largely intact.

Another aspect of the invention is further processing the "trim" to extract and isolate the trichomes there from. In such a process it is also desirable to minimize the extraction of cellulosic debris from the trim, as well as leaf cells components, such as chlorophyll.

It is a common practice in harvesting Cannabis to cut growing shoot or stalks having palm leaves and flowers, and then dry these shoots or stalk. The palm leaves can be removed, such as by cutting or manual pulling, before or after drying. The sugar leaves are typically removed after drying.

Another aspect of the invention is a method for trimming sugar leaves, other leaves and other undesirable plant matter the entire plant without drying. Avoiding drying saves space and time, as well as manual labor. It can also produce a Cannabis extract that retains essentially all the Cannabidiol (CBD) produced by the plants. CBD is one of at least 113 active cannabinoids identified in cannabis and can account for up to 40% of extracted plant resin. However it deteriorates rapidly with further processing, such as drying of the plants. CBD does not have any intoxicating effects and is component of several drugs under development or undergoing regulatory approval. Further, since such a Cannabis extract will also contain the A form of tetrahydrocannabinol (THC), which is not psychoactive (in contrast to the $\Delta^9$ form of THC) it can be used for medicinal purposes without the need to separate the THC. The A form of THC converts to the $\Delta 9$ form rapidly as freshly cut Cannabis plant matter starts to dry.

The preferred modes of conducting these processes are described below with respect to versions of the inventive apparatus in which the filter 300 as supported on the support frame 200 has an internal capacity or volume of about 5-20 gallons, which respectively can be used to contain and process about 3-15 lbs. of plant matter, in the case of Cannabis, as well as any other plant species in which the glandular trichome produce resin that is desirable to separate for further processing or direct use. To accommodate such loads of materials and sizes support frames the motor can have a speed range of about 10 to 40 RPM. A preferred apparatus has 3 discrete speeds of 15, 25 and 35 rpm, and deploys a motor is capable of providing the same torque at these speed to accommodate partially filling the chamber with water or another liquid, that is up to about 5-15 gallons, as well as the above weights of plant matter. More preferably the motor is capable being selectively operative to spin in opposite directions, and not in just a single direction.

It has been discovered that for the above capacity ranges, rotation speeds lower than about 10-15 rpm are not effective, while speed higher than about 35-40 rpm apply excessive centrifugal force. This excessive centrifugal urges the plant material toward the filter member 300 where it is retained.

It is desirable to deploy a speed range in which the plant matter mixes and tumbles with each rotation of the filter member 300.

The mixing and tumbling are beneficially enhanced by several means. One such means is the spacing of the posts 240 of the support frame 200 as described above. Another means to improve agitation, mixing and tumbling is to add discrete pieces of non-plant matter that is inert and durable. Golf ball sizes spheres with a diameter of 0.5 to 2 inches are effective. In particular ordinary golf balls have both the desired size and density, which is mass, as well as inertness to be used in the various separation processes disclosed herein. It has been discovered that about 3 to 6 golf balls or similar size tumbling agent are effective in a 5 gallon chamber, while about 6-9 are effective in a 20 gallon chamber. The tumbling aids should not be so hard and/or massive that at the desired speed they would damage the material that forms the filter 300. The balls or tumbling agents aid not only in breaking up material but also liberates any buildup of trichomes on the mesh or screen.

In a preferred trimming process while the plant matter is tumbling within the closed space of the filter 300 an inert freezing agent, such as one of liquid carbon dioxide and liquid nitrogen, is introduced therein in a quantity, rate and volume sufficient to rapidly reduce the temperature to about zero ° F. When an inert gas such as liquid carbon dioxide is introduced at a temperature of about −100 to −110° F. this temperature drop occurs in about 20 seconds to 2 minutes. The rapid temperate drop from injecting liquid $CO_2$ is believed to both purge oxygen and rapidly freeze residual moisture in the one or more of the leaves, bracts and bracteoles causing the fragmentation thereof to separate it from the desirable portions of the plant matter, which are the buds and flowers. When the filter 300 has mesh opening of about ¼ in. to ½ in, this fragmented plant matter on continued tumbling then traverses the mesh opening of the filter while the filter 300 retains a residual portion of the flowers.

The use of liquid freezing agents also removes surface molds and fungus, and is believed to kills *E. Coli* bacteria. The expanding gas also purges oxygen, preventing degradation of the cannabinoids during processing, and in the case of freshly cut cannabis, that is uncured plant matter, also prevents the conversion of the A form of THC to $\Delta^9$ THC, as well as the loss of the desirable CBD and potentially other cannabinoids of medicinal value.

It been discovered that after such trimming to remove sugar leaves, the residual flowers can then be processed again by changing the filter 300 to one having a smaller mesh size of less than about 25 to 200 microns to separate the trichome glands that are swollen the large resin content from the cellulosic plant matter in the buds and flower. The mesh is selected in accordance with the trichomes or other plant matter size that is intended to be separated from the other plant matter, which can be larger or smaller depending on the plant species and state of maturity, as well as if the intent is to separate other plant materials, such as pollens or seeds.

In the case of processing the flower and buds that have been trimmed form Cannabis plants, the inert freezing agent is preferably introduced at a quantity, rate and volume sufficient to rapidly reduce the temperature to about −60° F. When an inert gas such as liquid carbon dioxide is introduced at a temperature of about −1100 to −110° F. this temperature drop occurs in about 2-3 minutes. The rapid temperate drop from injecting liquid $CO_2$ rapidly freezes the flowers and bud such that the resin filled trichomes break free and separate, and also become harden and less sticky as the viscous resins therein solidify. This process can be completed in additional 5-15 minutes of turning or rotating the container 311, after the initial 2-3 of turning or rotating the container 311 during the phase of cooling about −60° F. More specifically it generally requires about 1-3 minutes of additional turning or rotating per lb. of material. The process generates a resin, or at least a resin rich concentrate, commonly known as kief for Cannabis resin extracts. The prior trimming process of the uncured leaves takes only about 30 seconds to a minute of additional turning or rotating per lb. When desired, dry or cured plant matter can also be trimmed or sugar and palm leaves by the first step as described above for green or uncured plant matter.

It should be noted that an unexpected result of using a liquid freezing agent is the discovery of temperature ranges that can selectively fracture sugar and palm leaves, for removal, without significantly disintegrating the flower and buds, while a lower temperature is effective in disintegrating the flower and buds to the extent necessary to liberate the resin bearing trichomes. This enables full processing of Cannabis and other plant species immediately after harvest when in the uncured state to extract useful materials, such as CDB and THC-A without degradation.

Liquid $CO_2$ can be used or metered from compressed gas tanks with the manually opening of the main gas valve, which is preferably connect to an insulated high pressure rated hose line leading to the chamber 100, and more preferred fed to the chamber via a coupling or portal in the chamber 100, the support frame 200, but preferably directly into the container 311 of the plan matter.

Sufficient freezing rates to reduce the environment of the plant matter to about −60° F. can be obtained with about 15 lbs of plant matter in a 20 gallon capacity chamber in about 3 minutes from a tank of liquid $CO_2$ compressed to about 800 psi, utilizing about 25 lbs. of the $CO_2$. Such tanks can be used even when the pressure drops to about 250 psi from prior process use. An adequate flow rate of liquid $CO_2$ can be obtained by measuring the tank weight loss, which for the above parameters is about 8 lbs./minute. Alternatively, or additionally the temperature can be monitored inside the chamber. Approximately about 5-8 lbs. of liquid $CO_2$ would be sufficient for "trimming" about 3 lbs. of plant matter in a 5 gallon capacity chamber. Alternatively, about 8-15 lbs. of liquid $CO_2$ can be used for trimming about 5 to 10 lbs. of plant matter in a 20 gallon capacity chamber. Trimming separation vs. the production of trichome resin glands, kief, from the separated flower and bud, requires about 70-75 percent less liquid $CO_2$ Thus, it is likely that about 1.5 to 4 lbs. of liquid $CO_2$ are required per pound of plant matter. It should be appreciated as a smaller capacity chamber has a larger surface area to volume ratio, the higher consumption of liquid $CO_2$ may be due to heat losses. It is expected that the consumption of the $CO_2$ could be reduced to improve efficiency at lower environmental chamber, but more preferably with thermal insulation of the chamber and/or using larger chambers. Colder inert liquids, such as liquid nitrogen may also require less inert freezing agent relative to the consumption of $CO_2$ reported above. Preferred rates of temperature drop and liquid freezing agent consumption can be readily developed using the above ranges as general guidelines. Liquid nitrogen and liquid $CO_2$ are examples of preferred liquid freezing agents, being compressed gases, they disperse on heating toward room temperature, and readily available. Other compressed gases can be used to provide liquid freezing agents, such as argon, helium, neon and the like. It should be appreciated that if a gasket is used to seal the chamber, it should either be configures to slowly vent the expanding gas, or more preferably a safety pressure release valve should be deployed on the chamber 100.

In another embodiment of the invention, an inert freezing agent may be solid $CO_2$, commonly known as dry ice. However, it is less desirable because it does not provide the rapid chilling that causes fragmentation of the sugar leaves, which enables the novel trimming process discussed above. Dry ice can be used in the inventive apparatus to the extent one is processing material that is already trimmed, or using trimmed sugar and/or palm or big leaves to further extract the trichome that a represent at a lower density, The various embodiments of the inventive apparatus can be used with dry ice, which for most forms of plant matter in which it is desirable to have cold processing, are preferably in the form of pellets or chips up to about a 0.5 in. in the maximum dimension, as well as with larger circa 0.5 to 2 inch square size cubes or comparable or larger sized balls. Smaller pellets or chips are more effective in chilling material rapidly, such as to solidify and harden viscous or sticky resin components, such as the product of the glandular trichomes which remain attached thereto, while larger ball or cubes are helpful agitating agents. Small pellets and larger cubes or balls of dry ice can be used together. Balls and other agitation means also adding in precluding a gradual build up of the resin on the exterior of the mesh or filter, as more trichome resin particles pass through the holes therein. Having made these discoveries, it will now be appreciated that other agitation means can also accomplish this goal, such as vibration and/or impact with balls or other instruments on the exterior of the filter mesh where the buildup can occur.

Further, any of the above methods of using solid or liquid freezing agents can be uses to fracture plant matter and harden trichome resin before adding water and other fluids to enhance the tumbling and mixing of material in the rotating chamber that improves the sieving efficiency.

Figure 12:
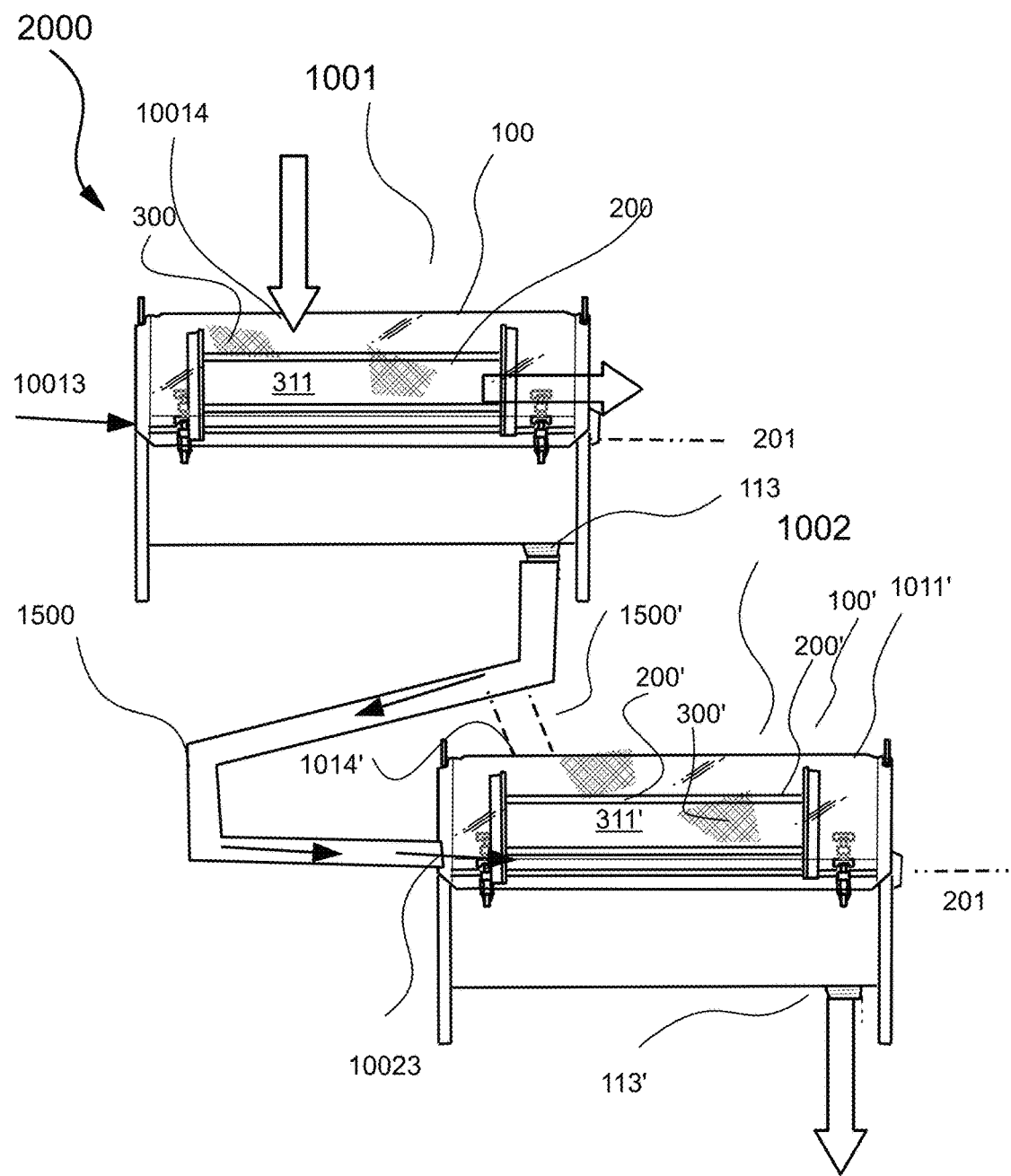
FIG. 12 is a schematic diagram illustrating an alternative embodiment of the invention using 2 or more of the inventive apparatus in a variety of inventive processes or methods.

Another preferred aspect of any of the above processes is process and apparatus illustrated in FIG. 12, in which first and second extractor are connected for use in series. As a non-limiting example of such use, fragmented leaves, bracts and bracteoles, which may be primary sugar leaves of Cannabis, separated in a first rotary extractor 1001 undergoes further processing in a second rotary separator 1002 to extract the trichomes there from. In such an embodiment it is also preferred that the separation method deploy a first and second horizontal axis rotary separation apparatus, each having a chamber 100 or 100' having an inlet port 10013 or 10023 at the side and an outlet or drainage port 113 and 113' at the bottom, a rotating filter support frame 200 adapted to rotate about a cylindrical axis 201 thereof to provide a cylindrical cavity defined by a connected upper and lower cylindrical base, a filter member 300 or 301' adapted to form an enclosed space or container 311 over the filter support frame 200 and 200' a rotary drive means adapted to turn or rotate the rotating filter support frame 200 and 200' about a primary axis 201 thereof that is disposed in a horizontal plane.

The rotary drive means in any embodiment can be a separate motor on each apparatus, or one motor connected by gears, chains, pulleys and/or direct to both chambers, such as but not limited or embodiment in FIG. 1-11.

The outlet port of the first horizontal axis rotary separation apparatus is connect to the inlet port of the second horizontal axis rotary separation apparatus. The inlet port is through a side wall for admitting effluent, namely fracture "trim" into the second enclosed space of the second cylindrical cavity.

In using this configuration of apparatus 2000, A method of plant matter separation may comprise the steps of admitting plant matter to the enclosed space or container 311 of the first horizontal axis rotary separation apparatus, rotating the rotating filter support frame of the first and second horizontal axis rotary separation apparatus and collecting a purified effluent from the outlet 113' at the bottom of the chamber 100' of the second horizontal axis rotary separation apparatus 1002.

In this method and apparatus, the filter member 300 of the first horizontal axis rotary separation apparatus 1001 has a larger opening size than the filter member 300' of the second horizontal axis rotary separation apparatus 1002, such as to enable the release of fractured trim. Water or another fluid is used to flush fragmented matter into the second horizontal axis rotary separation apparatus, via a connecting conduit 1500. The conduit 1500 can connect to the side entry portal 10023 to directly feed material separated in chamber 100 the container 311' of chamber 100'. Alternatively the conduit can be configured as 1500' to add fluid or gas to the cavity 1001' of chamber 100', such as via the lid. Similarly fluid or gas can be added to chamber 100 via portal 10013, directly to container 311, or via an upper portal 10014. Chamber 100' is shown with an optional upper penetration 10014' for the same purpose, as well as to optionally connect conduit 1500'. The filter member 300' of the second horizontal axis rotary separation apparatus may have a circa 25 to 200 micron mesh opening size to retrain the fractured trim, but allow the passage through the mesh of the smaller glandular trichomes that were on the sugar and/or palm leaves (or some small fraction that may have been released from the flowers and bud in the trimming process) and had been released there form by the combination of additional agitation and or fragmentation in the tumbling process such as from inert balls and/or dry ice.

Any combination of dry tumbling, tumbling with mixtures of water or other fluid and agitation balls or dry ice, liquid $CO_2$ or liquid nitrogen can be used in either the first or second chamber, and can be introduced at any inlet port or via the open bag.

The configuration of FIG. 12 can also be used when it is desired to separate plant or other matter into materials of 2 or 3 size ranges, such as when the objective of the separation process is to separate trichomes by size range, or separate trichomes from "trim" or extract additional trichomes from "trim" or larger leaves. The filters 300 and 300' are selected to provide the desired size of the opening in the mesh thereof.

It should also be understood it is not essential to dry the plant matter before the "trimming" process. A potential advantage of not drying or using so called "green", "wet" or uncured plant matter, is that the inventive process avoid the loss of CBD and the decarboxylation of A type THC, which converts it to more psychoactive form; trans-$\Delta^9$THC. Avoiding this decarboxylation results in product that is richer in non-psychoactive cyclic terpenes, such a CBD, which have other medicinal properties being mimetic of endocannabinoids and their activity with cannabinoids receptors.

The use of liquid $CO_2$ in various embodiments of the extraction process yielded unexpected improvements. First, when trimming at the preferred temperatures, the sugar leaves would fragment without damaging the plant buds and flowers. Hence, using mesh screen with opening in the range form about ¼ inch (6 mm) to about ½ inch (12 mm) these plant fragments would exit the container, while the buds and flower that are rich in trichomes would remain in the chamber defined by the mesh screen. While some trichomes are released in the process and separate out of the container 311 with the fragmented leaves, this material can be processed again using smaller mesh screens of about 25 to 200 microns holes to separate out the solid trichome resin glands. As different plants and stages of growth result in different size and shape trichome, the size of the holes in the mesh is selected according the size of the desired product to maximize speed, yet minimize and transfer of undesirable material.

The liquid $CO_2$ or liquid freezing agent process also significantly reduces the process times, compared with a comparable manual dry trimming process, which might run for 2 to 24 hours to achieve the desired separation. With the liquid $CO_2$ or other liquid freezing agent process, equivalent yields from the same plant material are achieved in 15 minutes. It should be appreciated that while the liquid $CO_2$ or other liquid freezing agent process has the greatest advantage in trimming green (uncured) or cured (dry) plant matter, it can be used in any other separation method. For example, the flowers and buds can be further processed in the same type apparatus in a manner that deliberately release trichome resin beads from this material, where the undesired plant material remains in the drum, but the small free glandular trichomes exit the chamber through a screen having a mesh size of about 25 microns to about 200 microns.

The inventive apparatus can also be used to remove the remaining trichomes on the "trim" material produced by manual, that is hand trimming or the inventive liquid freezing agent process. Manual or such processed trimmed leaves, that is sugar and/or the bigger palm leaves of can be reprocessed with the above liquid freezing agent method. Further water, dry ice, tumbling balls can also be used as a medium to release the trichome beads that are resin rich from any type of plant matter.

Another surprising improvement with the inventive apparatus compared with liquid wet sieving with bags is the faster speed of draining water through a fine mesh bag can take 30 minutes to about 12 hours, while in the inventive apparatus the flush an equivalent amount of water in 5 to 10 minutes for an about 6 to ×24 advantage in speed.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

We claim:

1. A method of plant matter separation comprising the steps of:
    a) providing at least a first horizontal axis rotary separation apparatus, having;
        i) a chamber having an inlet port and an outlet at a bottom,
        ii) a rotating filter support frame adapted to rotate about a cylindrical axis thereof to provide a cylindrical cavity defined by a connected upper and lower cylindrical base,
        iii) a filter member adapted to form an enclosed space over the filter support frame,
        iv) wherein the inlet port is adopted to deliver product to be separated into the enclosed space
        v) a rotary drive means adapted to turn the rotating filter support frame while a primary axis thereof is disposed in a horizontal orientation,
    b) admitting plant matter to the enclosed space of the first horizontal axis rotary separation apparatus,
    c) turning the rotating filter support frame of the first horizontal axis rotary separation apparatus,
    d) admitting at least one of water, dry ice, liquid carbon dioxide and liquid nitrogen to the enclosed space,
    e) collecting a purified plant matter effluent that is separated from the admitted plant matter from the outlet at the bottom of the chamber of the first horizontal axis rotary separation apparatus.

2. The method of claim 1 wherein said step of admitting at least one of water, dry ice, liquid carbon dioxide and liquid nitrogen to the enclosed space occurs before the step of turning the rotating filter support frame of the first horizontal axis rotary separation apparatus.

3. The method of plant matter separation according to claim 1 further comprising the steps of providing a second filter member in suspension within the filter support frame and said step admitting plant matter to the enclosed space of the first horizontal axis rotary separation apparatus comprises admitting the plant matter in the second filter member.

4. A method of plant matter separation comprising the steps of :
    a) providing a first and second horizontal axis rotary separation apparatus, each having;
        i) a chamber having an inlet port at the side and an outlet port at a bottom,
        ii) a rotating filter support frame adapted to turn in rotary motion about a cylindrical axis thereof to provide a cylindrical cavity defined by a connected upper and lower cylindrical base,
        iii) a filter member adapted to form an enclosed space over the filter support frame,
        iv) wherein the inlet port is adopted to deliver product to separated into the enclosed space
        v) a rotary drive means adapted to rotate the rotating filter support frame about a primary axis thereof that is disposed in a horizontal plane,
        vi) wherein the outlet port of the first horizontal axis rotary separation apparatus is connect to the inlet port of the second horizontal axis rotary separation apparatus,
    b) admitting plant matter to the enclosed space of the first horizontal axis rotary separation apparatus,
    c) turning the rotating filter support frame of the first and second horizontal axis rotary separation apparatus,
    d) collecting a purified effluent from the outlet port at the bottom of the chamber of the second horizontal axis rotary separation apparatus.

5. The method of plant matter separation according to claim 4 wherein the filter member of the first horizontal axis rotary separation apparatus has a larger opening size than the filter member of the second horizontal axis rotary separation apparatus.

6. The method of plant matter separation according to claim 4 wherein a liquid freezing agent is injected into an enclosed space over the filter support frame of the first horizontal axis rotary separation apparatus and water is then injected to flush a product from the first outlet port to an inlet port of the second horizontal axis rotary separation apparatus.

7. The method of plant matter separation according to claim 6 further comprising using a one or more of dry ice and balls to improve agitation in enclosed space over the filter support frame of the second horizontal axis rotary separation apparatus.

8. A method of processing plant matter, the process comprising:
 a) providing a mixture of plant matter that includes flowers and flower buds and at least one of leaves, bracts and bracteoles, flowers and buds containing calyxes and sugar leaves,
 b) placing the mixture in a closed spaced bounded on at least one side by a mesh member, wherein the mesh member has a spacing sufficient to retain the mixture of plant matter,
 c) tumbling the mixture within the closed space,
 d) introducing a liquid freezing agent into the closed space,
 e) wherein residual moisture in the one or more of the leaves, bracts and bracteoles freezes causing the fragmentation thereof such that the fragmented plant matter traverses the mesh member and the closed space retains a residual portion of the flowers.

9. The method of processing plant matter according to the claim 8 wherein the plant matter is from the species cannabis and the residual portion is primarily calyxes.

10. The method of processing plant matter according to the claim 8 wherein the fragmented plant matter includes one or more of fan leaves and sugar leaves.

11. The method of processing plant matter according to the claim 8 wherein the closed space is a cylinder having a first circular plate at a top and a spaced apart second circular plate as a bottom, wherein the first and second circular plate are connected by a cylindrical wall that is at least partially covered by the mesh member.

12. The method of processing plant matter according to the claim 11 wherein the circular top and bottom are connected by spaced apart rods disposed between a center of the cylinder and the cylindrical wall.

13. The method of processing plant matter according to the claim 8 wherein one of the liquid carbon dioxide and liquid nitrogen are introduced to the closed space as a jet from a center of one of the first and second circular plate wherein the jet of an expanding gas impinges on the other circular plate to disperse within the plant matter.

14. The method of processing plant matter according to the claim 11 wherein the cylinder is rotated to tumble the plant matter.

15. The method of processing plant matter according to the claim 11 wherein one of the liquid carbon dioxide and liquid nitrogen are introduced to the closed space as a jet from a center of one of the first and second circular plates.

16. The method of processing plant matter according to the claim 8 further comprising a step of adding balls to the closed space to facilitate the tumbling of the mixture.

17. The method of processing plant matter according to the claim 8 wherein the mesh member has holes with a diameter of about 0.25 inches to about 0.5inches.

18. The method of processing plant matter according to the claim 8 further comprising the additional steps of:
 a) terminating the tumbling of the plant matter,
 b) removing the remaining plant matter that consists essentially of buds and flowers, and
 c) further processing the buds and flowers to remove resin bearing trichomes therefrom.

19. A method of processing plant matter, the method comprising:
 a) providing a mixture of plant matter that includes flowers and flower buds and at least one of leaves, bracts and bracteoles,
 b) placing the mixture in a confined space,
 c) tumbling the mixture within the confined space,
 d) introducing an inert freezing agent into the confined space
 e) wherein residual moisture in the one or more of the leaves, bracts and bracteoles freezes causing the fragmentation thereof such that a resulting fragmented plant matter is smaller in size than the flower buds.

20. The method of processing plant matter of claim 19 wherein the confined space has a plurality of opening such that the fragmented plant matter traverses the openings and the confined space retains a residual portion of the flowers.

21. The method of processing plant matter of claim 19 further comprising providing an outer container around the confined space to collect the fragmented plant matter.

22. The method of processing plant matter of claim 19 wherein the inert freezing agent is a liquid freezing agent.

* * * * *